United States Patent [19]

Nave

[11] Patent Number: 4,886,057
[45] Date of Patent: Dec. 12, 1989

[54] ASSISTED BREATHING INTERFACE DEVICE

[75] Inventor: Jerald L. Nave, Colorado Springs, Colo.

[73] Assignee: E Z Breathe, Inc., Colorado Springs, Colo.

[21] Appl. No.: 126,420

[22] Filed: Nov. 30, 1987

[51] Int. Cl.[4] ............................................. A61M 16/00
[52] U.S. Cl. ............................ 128/203.11; 128/202.28
[58] Field of Search ...................... 128/202.28, 202.29, 128/203.11, 205.24, 207.16

[56] References Cited

U.S. PATENT DOCUMENTS

| | | | |
|---|---|---|---|
| 3,286,710 | 11/1966 | Bartlett, Jr. ...................... | 128/203.11 |
| 3,548,822 | 12/1970 | Seeler .............................. | 128/203.11 |
| 4,106,502 | 8/1978 | Wilson ............................. | 128/203.11 |
| 4,520,811 | 6/1985 | White et al. ..................... | 128/203.11 |
| 4,697,587 | 10/1987 | Marinkovich ................... | 128/203.11 |

FOREIGN PATENT DOCUMENTS 2176406  12/1986  United Kingdom ........... 128/202.29

Primary Examiner—Edgar S. Burr
Assistant Examiner—Aaron J. Lewis
Attorney, Agent, or Firm—Timothy J. Martin; J. Preston Oxenham

[57] ABSTRACT

An assisted breathing interface device for use by emergency care personnel in administering artificial resuscitation of a patient includes a housing unit having an open interior first and orifices communicating with the interior and a vent structure communicating with the interior. The first orifice may be engaged by the mouth of the emergency care administrator and the second orifice may be inserted in and engaged by the mouth of the patient, with the vent structure exteriorly opening to the ambient environment. A valve structure is provided which, when opened, permits passage of air from the first orifice, through the interior and out of the second orifice. When closed, the valve structure prohibits air flow from originating at the second orifice to exit through the interior and out of the first orifice, but permits the air to exit to the ambient environment out of the vent structure. When open, the valve structure preferably restricts air flow from passing out of the interior by way of the vent structure. An auxiliary mouthpiece may be employed along with a ported washer as part of the first orifice. The housing unit may be of a two-piece, snap-fit construction including a main body and an end cap.

13 Claims, 3 Drawing Sheets

ASSISTED BREATHING INTERFACE DEVICE

FIELD OF INVENTION

The present invention is directed to an interface device which may be operatively used by first aid personnel or other emergency care administrators when performing artificial respiration on a patient. The device is constructed to protect such personnel from direct contact with the patient to reduce the risk of inhalation of air after it has been respirated by the patient. Thus the field of the present invention concerns medical devices which allow first aide personnel to perform a type of mouth-to-mouth resuscitation with reduced risk of contamination.

BACKGROUND OF INVENTION

One of the more recognized and effective first aid procedures in reviving accident victims is mouth-to-mouth resuscitation. This procedure is implemented for those patients who, for one reason or another, have either ceased respiratory functions or have only limited respiratory functions. Example of such patients include drowned victims, electric shock victims and other accident victims who have their respiratory systems traumatized. Such victims often need assistance, through artificial means, for respirating until the autonomic nervous system is again able to operate and control the respiratory system.

While elaborate respirating apparatus is usually available in hospital facilities, these accident victims often require immediate respiratory aid prior to being moved to established medical facilities. In the past, first aid personnel have relied on the technique known as "mouth-to-mouth resuscitation" as a means of performing artificial respiration on various traumatized accident victims. The mouth-to-mouth resuscitation technique is a procedure wherein the first aid personnel inhale air, places his/her mouth on the open mouth of the victim and the forcefully exhales the air into the victims lungs, thereby providing a source of replenishing oxygen for the victims circulatory system. Next, the first aid provider presses on the victims chest to force air out of the lungs thereby causing the victim to exhale, after which the cycle is repeated.

The success of the mouth-to-mouth resuscitation technique has proven its validity over the course of years so that its value as an emergency care procedure is unquestioned. However, in recent times, concern over the transmission of various diseases has caused emergency care administrators such as paramedics, police and the like to become reluctant to implement mouth-to-mouth resuscitation. Such personnel fear contracting a disease from the accident victim through contact with the person's saliva, mucous and exhaled air. Not the least of these fears has been the recent widespread appearance of that disease known as Acquired Immune Deficiency Syndrome, or AIDS, which is thought to be transmitted only through direct contact with the bodily fluids of the disease carrier. The fear of other communicable diseases which are thought to be readily transmitted by contact with another's bodily fluids or exhaled air stream is prevalent, as well.

Thus, while many emergency medical assistance personnel recognize the need to implement artificial respiration on accident victims, these persons are placed in a dilemma since, by attempting to save the victim's life, they may, themselves, contract a serious and even fatal disease. As a result, many medical personnel have declined to provide emergency mouth-to-mouth resuscitation. This in turn has lead to literally tens of thousands of deaths of accident victims who otherwise may have been saved through the artificial respiration technique.

Accordingly, a dramatic need has been recognized by the present invention for a simple medical device which can act as in interface between an emergency care administrator and a patient since that artificial respiration maybe given in a manner similar to mouth to mouth resuscitation while, at the same time, reducing the danger and fear of disease contamination from the patient. The present invention has been developed to address this need.

SUMMARY OF THE INVENTION

It is an object of the present invention to provide an air flow device which may be used by an emergency care administrators as an interface between themselves and their patients during the performance of artificial respiration.

It is a further object of the present invention to provide an inexpensive and disposable device used as an interface between emergency care administrators and an accident victim during mouth to mouth resuscitation which device prevents direct oral contact.

It is another object of the present invention to provide a respiratory device for use during the performance of artificial respiration by emergency medical personnel wherein the device provides a one way path for the exhaled air from the medical personnel into the patient yet which reduces the likelihood that air exhaled by the patient will be inhaled by the medical personnel.

It is a still further object of the present invention to provide a respiratory device such that a patient may inhale and exhale through the device thus receiving air either from the external environment or air from medical personnel yet which device prevents air exhaled by the patient from being inhaled by the medical personnel.

Yet a further object of the present invention is to provide an inexpensive disposable device that is simple in manufacture which device may be individually packaged and sterilizing for individual use with accident victims and which may be disposed after use to avoid contamination between victims and between emergency medical personnel.

According to the present invention, then, an assisted breathing interface device is provided and is adapted for use by an emergency care administrator in performing artificial respiration of a patient. In its broad form, this device includes a housing unit that has an outer wall enclosing a chamber. A first orifice is formed in the housing unit and is adapted to be engaged by the mouth of the emergency care administrator so that air may be blown through the first orifice into the interior of the chamber. A second orifice is formed on the chamber and is adapted to be inserted into and engaged by the mouth of the patient and is operative to permit air flow between the chamber and the patient. A vent structure is provided separately of the first and second orifices and establishes air flow communication between the interior of the chamber and the ambient environment external of the patient when the first orifice is engaged by the mouth of the emergency care administrator and when the second orifice is engaged in the mouth of the patient. A valve is provided in the housing unit with the valve being movable between an open position and a closed position for permitting air flow from the first orifice, into the chamber and out of the second orifice when the valve is in the open position and for substantially prohibiting air flow from the chamber into the first orifice when the valve is in the closed position. Preferably, this valve structure also restricts air flow from the chamber out of the vent structure when the valve is in the open position.

Further detailed features of the present invention are also described and include the specific construction of the orifices, the vent structure and the valve element. To this end, in preferred embodiment of the present invention, the housing unit is constructed as a cylinder having a surrounding sidewall and a pair of opposite end walls. The first orifice is formed as an opening in one of the end walls from which a tubular extension projects axially outwardly therefrom. Likewise, the second orifice is constructed as an opening in the opposite end wall from which a second tubular extension projects axially outwardly thereof. The vent structure is formed by a lateral opening in the sidewall of the housing and includes a tubular extension that projects inwardly of the housing and longitudinally therein to terminate in a mouth that is in spaced, facing relation to the first opening. The valve element can then conveniently be a flap valve having an annular portion surrounding the first opening and a flap that moves from a closed position wherein it is seated against the first end wall to seal the first opening and a second or open position. In the open position, the flap element permits air flow through the first opening and restricts flow of air from the first orifice into the vent tubular extension.

An auxiliary mouthpiece may also form part of the first orifice and may be matably received in the first orifice tubular extension. It is desirable, when the present invention is used in conjunction with the auxiliary mouthpiece, to include a limit stop to prevent the mouthpiece from contacting the valve element. This stop means may include a radially inwardly projecting ridge formed on an inner sidewall of the first orifice tubular extension and also may include the use of a ported washer that may be mounted in this tubular extension against the ridge. Furthermore, in the preferred construction, the first end wall is formed as a cap element which includes the first end wall and a longitudinally projecting rim adapted to receive the surrounding sidewall of the housing unit in mated engagement. To this end, also, an interlock structure may be provided between the rim and the surrounding sidewall so that the pieces snap-fit together.

These and other objects of the present invention will become more readily appreciated and understood from a consideration of the following detailed description of the preferred embodiment when taken together with the accompanying drawings, in which:

DETAILED DESCRIPTION OF THE PREFERRED EMBODIMENT

The present invention relates to emergency care devices which may be used for assisting the respiration of an accident victim, hereinafter referred to as a patient. Thus, the present device is particularly useful as an interface device employed during assisted breathing by an emergency care administrator and may readily be employed to allow such emergency care administrator to practice "mouth-to-mouth" resuscitation with reduced danger of the care administrator breathing exhaled air from the patient. Thus, the present invention reduces the danger of disease transmission from the patient to the emergency care administrator during the performance of artificial respiration.

Figure 1:
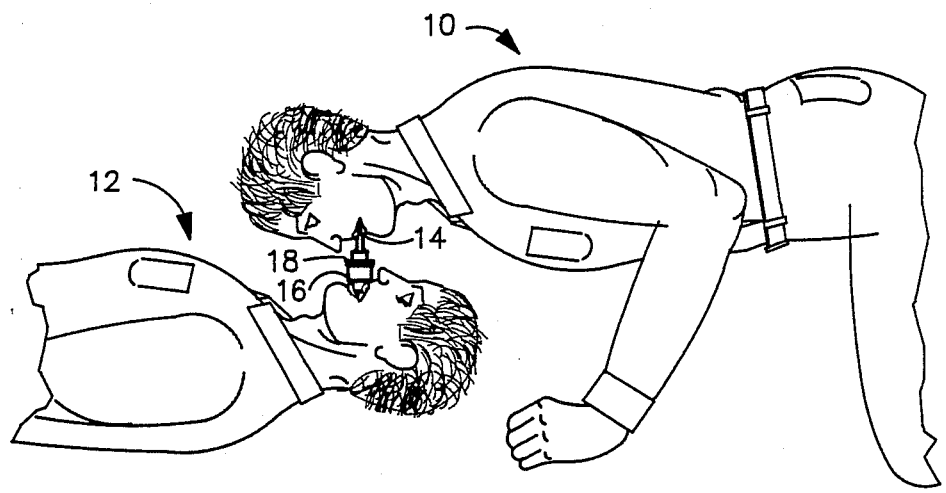
FIG. 1 is a side view in elevation showing an emergency care administrator utilizing the present invention to give artificial respiration to a patient.

As is shown in FIG. 1, the present invention is constructed as an assisted breathing interface device 18 which may be an interface between an emergency care administrator 10 and a patient 12 during the performance of artificial resuscitation. As is shown in FIG. 1, and as hereinafter more thoroughly described, interface device 18 includes a first orifice having an auxiliary mouthpiece that is engaged by the mouth 14 of the emergency care administrator 10 and a second orifice that is inserted in and engaged by the mouth 16 of patient 12. Emergency care administrator 10 may then exhale through device 18 to fill the lungs of patient 12 without oral contact with the patient 12. At the same time, device 18 vents air exhaled from the patient to the atmosphere so that this exhaled air is not breathed through the mouth of emergency care administrator 10.

Figure 2:
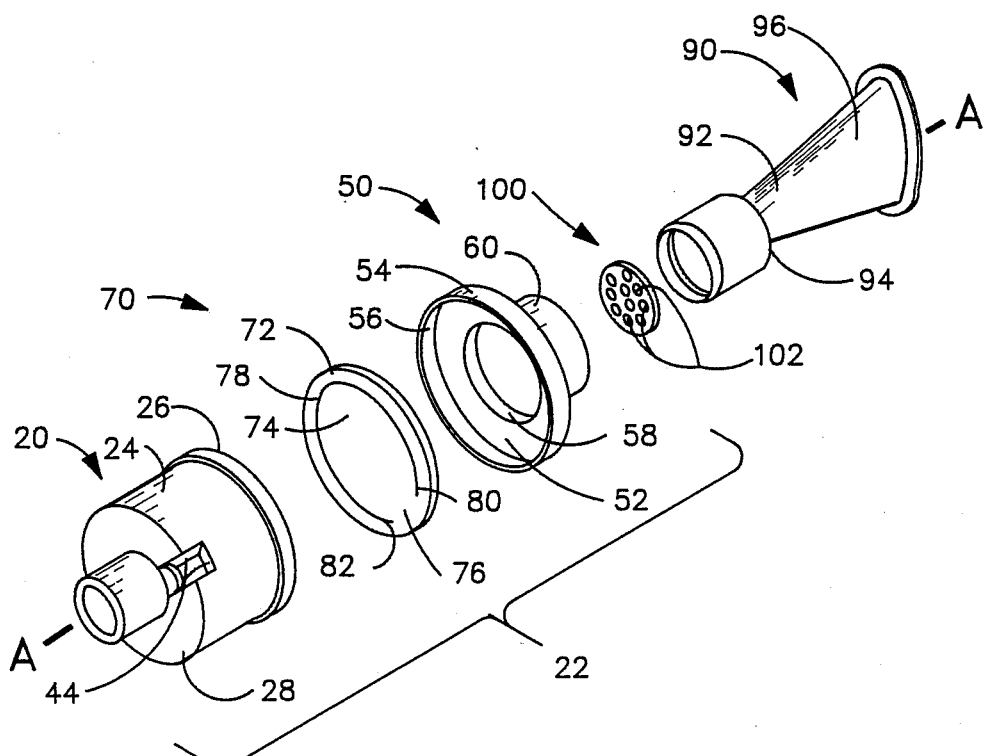
FIG. 2 is an exploded view in perspective of the component parts of the preferred embodiment of the present invention.

The component parts of the preferred embodiment of interface device 18 are best shown in FIG. 2. These component parts include a housing unit formed by a main body 20 and end cap 50, a flap valve 70, an auxiliary mouthpiece 90 and a ported washer 100. Device 18 is shown in an exploded view in FIG. 2 and in an assembled view in FIG. 3. As is shown in these figures, a main housing unit 22 is formed by main body 20 and end cap 50; housing unit 22 is configured to have a generally cylindrical shape. To this end, housing unit 22 has a surrounding sidewall formed by cylindrical sidewall 24 of main body 20. Sidewall 24 has a circular edge portion 26 that is matably received by cap member 50. To accomplish this, cap member 50 has a flat transverse wall 52 that forms a first end wall for housing unit 22 and a longitudinally extending rim 54 that receives edge portion 26. Thus, rim 54 is sized to receive edge portion 26 of main body 20 in close fitted, mated engagement. End cap 50 and main body 20 may be secured together in any convenient manner known in the art, including adhesives, spin welding, ultrasonic welding and the like. In the preferred embodiment, end cap 50 and main body 20 may be provided with cooperative interlocking structure such as outwardly projecting lip 30 formed on end portion 26 and inwardly projecting lip 54 formed on rim 52, as is best shown in FIGS. 4–6. Main body 20 includes a flat transverse wall 28 opposite edge portion 26 with flat wall 28 defining a second end wall for housing unit 22 opposite the first end wall. Accordingly, wall 52 and wall 28 may be respectively referred to as first end wall 52 and second end wall 28 for housing unit 22. The elements of interface device 18 are assembled along longitudinal axis "A".

Figure 3:
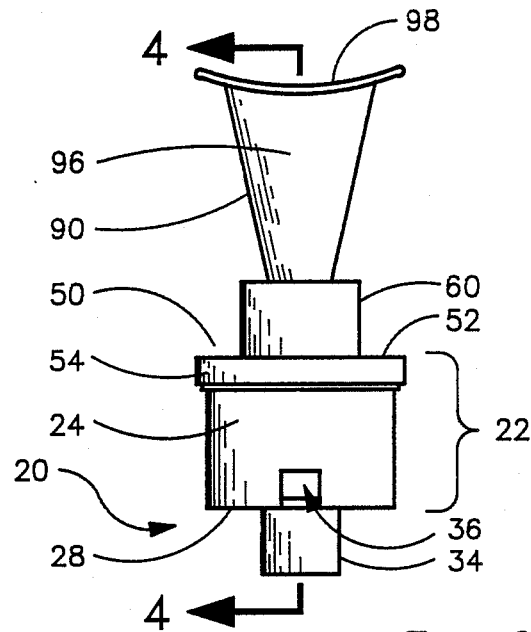
FIG. 3 is a side view in elevation of the preferred embodiment of the present invention.
Figure 4:
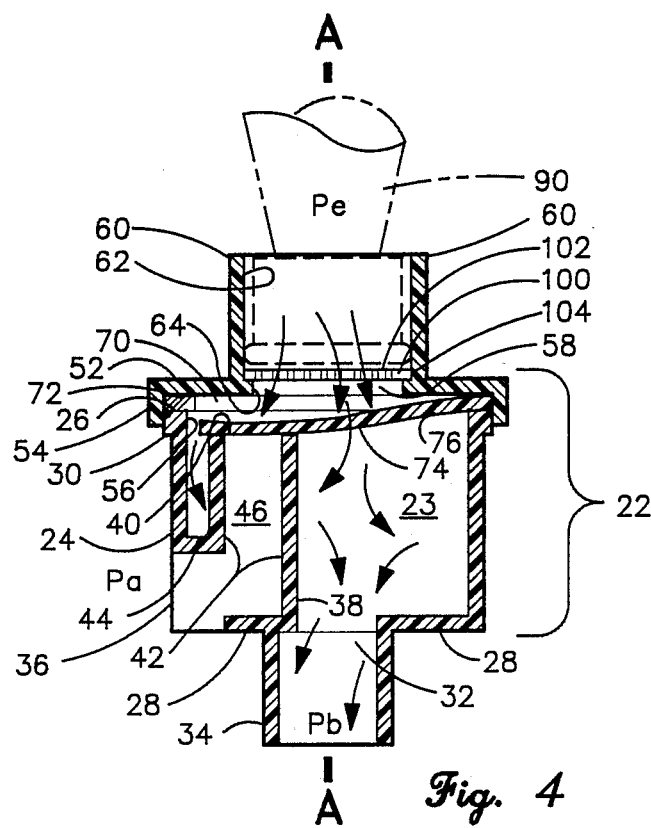
FIG. 4 is a cross-sectional view taken about lines 4—4 of FIG. 3 showing the valve structure in an open position and wherein an emergency care administrator is placing a positive pressure on the first orifice thereof.
Figure 5:
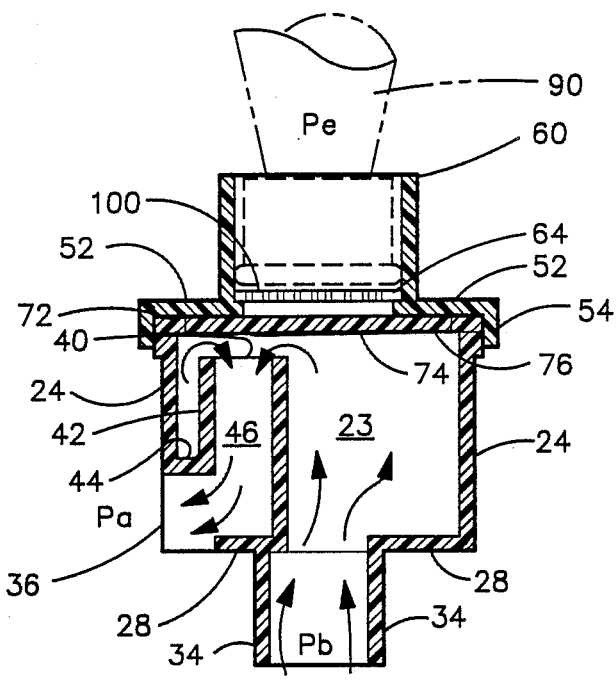
FIG. 5 is cross-sectional view similar to FIG. 4 but showing the valve structure in a closed position that occurs when a patient exhales through the device.
Figure 6:
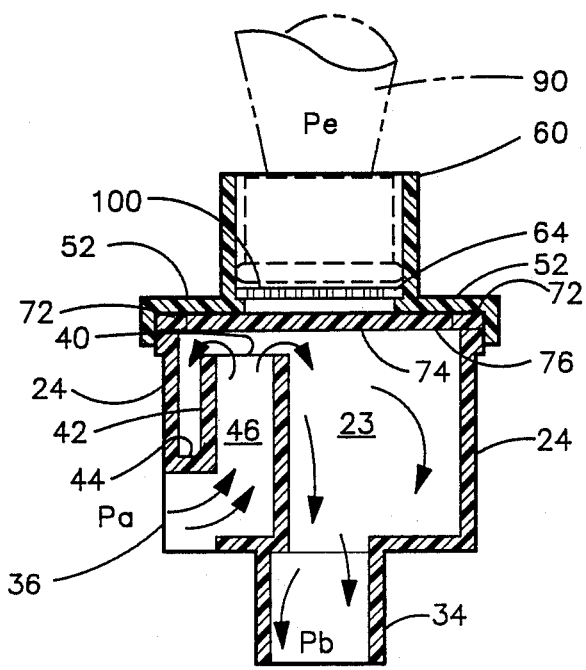
FIG. 6 is a cross-sectional view similar to FIGS. 4 and 5 showing the valve structure in a closed position wherein a patient inhales through the device.

While the individual pieces used to construct interface device 18 are shown disassembled in FIG. 2 and assembled in FIG. 3, the additional structure of interface device 18 may be further understood by reviewing the cross-sectional view of FIGS. 4-6. As is shown in these various figures, housing unit 22 is provided with a first orifice preferably formed by a first opening 58 located centrally of end wall 52 and a tubular extension projecting axially outwardly from housing unit 22. It should be appreciated that end wall 52 is thus annular in configuration with tubular extension 60 formed integrally therewith so that tubular extension 60 is in fluid communication with the interior 23 of housing unit 22 through opening 58. Housing unit 22 is provided with a second orifice adapted to be inserted in and engaged by the mouth of the patient. This orifice is preferably formed by a second opening 32 formed in second end wall 28 and a tubular extension 34 projecting outwardly from housing 22 in an axial direction. Tubular extension 34 is cylindrical in shape and surrounds opening 32 as an integral extension of end wall 28.

Housing unit 22 is provided with a lateral vent in the form of a third opening 36 formed in sidewall 24. Additional venting structure is provided in the preferred embodiment, however, in the form of a third tubular extension 42 which is in fluid communication with vent opening 36. Tubular extension 38 projects into the interior 23 of housing unit 22 and terminates in a mouth 40 in spaced facing relation to first opening 58. To this end, tubular extension 38 includes a longitudinal cylindrical tube section 42 having a sidewall which extends from mouth 40 to second end wall 28 and is connected to sidewall 24 by means of connecting walls 44 best shown in FIGS. 2 and 4-6. Accordingly, it should be understood that the connecting walls 44 and longitudinal tubular section 42 define an enclosed passageway 46 which vents the interior 23 of chamber 22 to the ambient atmosphere through opening 36.

A valve means is provided for permitting air flow through the first orifice into the interior of the chamber when it is in an open position and for substantially prohibiting air flow from the chamber into the first orifice in the closed position. While different types of valve means known in the art are contemplated by this invention, in the preferred form of the present invention, a diaphragm-type or flap valve 70 is provided as is best shown in FIG. 2. Flap valve 70 includes an outer annular portion 72 and a flap portion 74 which is hingedly connected at 76 to annular portion 72. To this end, flap valve 70 is constructed of a flexible material such as food grade rubber, with flap portion 74 being formed by a semi-circular cut 78 extending around a flap area from opposed first and second ends 80 and 82. Thus, hinge connection 76 is that region between opposed ends 80 and 82.

As is shown in FIGS. 4-6, flap valve 70 is mounted against wall 52 of end cap 50. It should be appreciated that semi-conductor cut 78 is of sufficient size so that flap portion 74 is larger in dimension that first opening 58 so that flap portion 74 completely covers 58 as it seats against wall 52 when the flap valve 70 is in the closed position, such as shown in FIGS. 5 and 6. To accomplish this mounting, flap valve 70 can be suitably adhered around annular portion 72 to wall 52. Additionally, in the preferred embodiment of the present invention, flap valve 70 is disc-shaped and sized so that it is in closed-fitted, concentric relation with rim 54 so that the outer peripheral margin 84 of annular portion 72 may be trapped between end portion 26 of sidewall 24 and annular wall 52.

It should be understood that flap valve 70 is movable between an open position shown in FIG. 4 and a closed position shown in FIGS. 4 and 6. In the open position shown in FIG. 4, air may flow through tubular first extension 60, around flap portion 74, through chamber 23 and out of tubular extension 34, as is shown by the flow arrows in that figure. Accordingly, when the emergency care administrator engages the first orifice with his/her mouth and exhales, a positive pressure $P_e$ is created at tubular extension 60, as is shown in FIG. 4. $P_e$ is greater than the ambient pressure, $P_a$, at opening 36. As noted above, the second orifice in the form of tubular extension 34 is inserted into the mouth of the patient so that opening 32 is at pressure $P_b$ which, absent any breathing by the patient is initially at ambient pressure. When the emergency care administrator forcefully blows air through tubular extension 60, flap portion 74 moves into the open position away from opening 58. It should now be understood that, with respect to the preferred embodiment of the present invention, as is shown in FIG. 4, the position of mouth 40 is selected along with the dimension of flap portion 74 so that, in the open position, an outer edge portion 86 of flap portion 74 rests against mouth 40 to substantially restrict any air flow out of the vent structure when flap valve 70 is in the open position. Thus, air freely flows from the emergency care administrator through chamber 23 and into the lungs of the patient. Other structure to accomplish this result is within the scope of this invention. For example, opening 36 could be constructed as a port in sidewall 24 and the emergency care administrator could manually block and unblock opening 36 with his/her fingers as necessary.

When the patient exhales, either voluntarily or through respiration pressure on the patient's chest, $P_e$ generally returns to the ambient pressure and $P_b$ is at a positive pressure greater than ambient, as is shown in FIG. 5. This creates an air flow shown by the flow arrows in FIG. 5. Here, the pressure in chamber 23 increases above ambient thereby seating flap portion 74 against wall 52 and closing opening 58; this substantially prevents air flow out of interior 23 through opening 58. However, when flap valve 70 is in the closed position shown in FIG. 5, the venting structure is opened so that free air flow out of interior 23 occurs through passageway 46 and opening 36. This process may be repeated by the emergency care personnel as needed.

At such time that a patient begins to inhale on his/her own, an air flow occurs as is diagrammed by the flow arrows in FIG. 6. Here, when the patient inhales, $P_b$ is at a pressure below ambient while $P_e$ is generally at ambient pressure. In this situation, air flows into the interior 23 of housing unit 22 through opening 36 and passageway 46 where it may then be drawn through tubular extension 34 by the patient. This air flow increases the pressure in interior 23 above the ambient pressure so that flap valve 70 again seats in the closed position.

Accordingly, it should be appreciated that whenever the pressure at the first orifice is positive and the vent means is at ambient pressure and where the second orifice is at a second pressure less than the positive pressure of the first orifice, the valve is in the open position. However, whenever the pressure at the second orifice is greater than the pressure at the first orifice, the valve moves to the closed position. Furthermore, the valve is in the closed position whenever the first pressure at the first orifice is below the ambient pressure and the vent means is at ambient pressure. This, then, allows the emergency care administrator to exhale air directly into the patient but the care administrator is protected against any inhalation of air that is subsequently exhaled by the patient.

In the preferred embodiment of the present invention, as noted above, an auxiliary mouthpiece 90 is provided as part of the first orifice to be engaged by the mouth of the auxiliary care provided. As is shown in FIGS. 2 and 3, and as is shown in phantom in FIGS. 4–6, auxiliary mouthpiece 90 includes a cylindrical tubular first end portion 92 that includes an outwardly projecting shoulder 94 sized for close fitting insertion into the interior of first tubular extension 60 along interior sidewall 62 thereof. A second end portion 96 of auxiliary mouthpiece 90 is formed by flattening an extension of tubular first end portion 92 so that second end portion 69 has an oval cross section which better conforms to the shape of the human mouth. To this end also, end portion 96 terminates in a lip 98 opposite shoulder 94 so that auxiliary mouthpiece 90 may be more conveniently engaged by the mouth of the emergency care administrator.

Auxiliary mouthpiece 90 is inserted into tubular extension 60. In order to prevent interference by mouthpiece 90 with flap valve 70, a radially inwardly projecting ridge 64 is formed on inner sidewall 62 of tubular extension 60. In the preferred embodiment of the present invention, this a disc-shaped ported washer 100 is provided. Washer 100 has a plurality of air ports 102 formed therein, and it is received inside tubular extension 60 such that its outer perimeter 104 rests against ridge 64 on a side opposite opening 58. Ridge 64 and washer 100 provide a limit stop against which shoulder 94 may abut as it is advanced into tubular extension 60 thereby preventing end portion 92 from extending through opening 58. Washer 100 is thus trapped between first end portion 92 of mouthpiece 90 and ridge 64. Ported washer 100 prevents any large particulate matter from being blown by the emergency care administrator into the mouth of the patient and further prevents undesired advancement of mouthpiece 90 into an interfering position with flap valve 70.

Based on the foregoing, it should be appreciated that the present invention is inexpensive in construction since most of the parts may be formed out of injection molded plastic. Thus, this device may be produced in a very economical manner and packaged as individual, sterilized units in packages that may be opened by the emergency care administrator at an onsight location for administering artificial resuscitation. After use, due to the inexpensive nature of this product, the device may be discarded so that there is no risk of patient-to-patient contamination through multiple usages.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. An assisted breathing interface device adapted for use by an emergency care administrator in performing artificial respiration of a patient, comprising:

a housing unit having an outer wall enclosing a chamber having an interior and including a first orifice lying in a first plane adapted to be engaged by the mouth of the emergency care administrator whereby air may be blown through the first orifice and into said chamber by the emergency care administrator and including a second orifice adapted to be inserted into and engaged by the mouth of the patient and operative to permit air to flow between said chamber and patient;

vent means for establishing air flow communication between said chamber and the ambient environment external of the patient when the first orifice is engaged by the mouth of the emergency care administrator and when the second orifice is engaged in the mouth of the patient, said vent means including an enclosed extension passageway within said chamber, said passageway terminating at a second plane parallel to said first plane to form a mouth with its entire perimeter lying in said second plane and in opposing relation to said first orifice;

valve means movable between a first position and a second position for permitting air flow through the first orifice and into said chamber in the first position and for substantially prohibiting air flow from said chamber into said first orifice in the second position.

2. An assisted breathing interface device according to claim 1 wherein said valve means restricts air flow from said chamber out of said vent means when said valve means is in the first position.

3. An assisted breathing interface device according to claim 2 wherein a positive first pressure at said first orifice when said vent means is at ambient pressure and said second orifice is at a second pressure less than the positive first pressure causes said valve means to be in the first position.

4. An assisted breathing interface device according to claim 3 wherein said valve means moves to the second position when the second pressure is greater than or equal to said first pressure.

5. An assisted breathing interface device according to claim 2 wherein said valve means moves to the second position whenever a first pressure at said first orifice is below ambient pressure and said vent means is at ambient pressure.

6. An assisted breathing interface device according to claim 1 wherein said first orifice includes a first opening in a first wall portion of said housing, said valve means includes a flap valve element having an annular portion surrounding said first opening and having a movable flap portion hingedly connected to said annular portion such that said flap portion is seated across said first opening in substantially sealed relation with respect to the first wall portion when said valve is in the second position and said flap portion is located away from said first opening when said valve is in the first position.

7. An assisted breathing interface device according to claim 6 wherein said annular portion is adheringly affixed to said first wall portion completely around said first opening.

8. An assisted breathing interface device according to claim 6 wherein said flap valve element is constructed as a panel of food grade rubber and wherein said flap portion is formed by a cut extending around a selected flap area of said flap valve element from opposed first and second ends, such that a region of said flap valve element between said first and second ends defines a flexible hinge for said flap portion.

9. An assisted breathing interface device according to claim 6 wherein said first orifice includes a first tubular extension projecting outwardly from said housing an in fluid communication with said first opening.

10. An assisted breathing interface device according to claim 9 including an auxiliary mouthpiece member defining an air flow passageway between a first mouth piece end insertable into the mouth of the emergency care administrator and a second mouthpiece end engaging said first tubular extension.

11. An assisted breathing interface device according to claim 9 wherein said second orifice includes a second opening in a second wall portion of said housing and a second tubular extension projecting outwardly from said housing and in fluid communication with said second opening.

12. An assisted breathing interface device according to claim 6 wherein said vent means includes a third opening in a third wall portion of said housing and said enclosed extension passageway comprises a third tubular extension projecting into the interior of the chamber and said mouth lies in a plane which is parallel to a plane defined by said first orifice.

13. An assisted breathing interface device according to claim 12 wherein said flap portion covers said inner mouth to restrict air flow from said chamber through said third tubular extension and out of said third opening when said valve is in the first position.

* * * * *